(12) United States Patent
Ries et al.

(10) Patent No.: US 10,667,846 B2
(45) Date of Patent: Jun. 2, 2020

(54) DEVICE FOR FIXATING A ROD TO A BONE

(71) Applicant: JOIMAX GMBH, Karlsruhe (DE)

(72) Inventors: Wolfgang Ries, Linkenheim-Hochstetten (DE); Lars Schendzielorz, Linkenheim-Hochstetten (DE); Alexander Dürr, Tamm (DE)

(73) Assignee: JOIMAX GMBH, Karlsruhe (DE)

( * ) Notice: Subject to any disclaimer, the term of this patent is extended or adjusted under 35 U.S.C. 154(b) by 104 days.

(21) Appl. No.: 15/766,179

(22) PCT Filed: Sep. 1, 2016

(86) PCT No.: PCT/EP2016/001479
§ 371 (c)(1),
(2) Date: Apr. 5, 2018

(87) PCT Pub. No.: WO2017/059941
PCT Pub. Date: Apr. 13, 2017

(65) Prior Publication Data
US 2018/0296250 A1  Oct. 18, 2018

(30) Foreign Application Priority Data

Oct. 6, 2015 (DE) .................. 10 2015 012 909
Jun. 30, 2016 (DE) ................. 20 2016 004 114 U

(51) Int. Cl.
*A61B 17/70* (2006.01)
*A61B 17/86* (2006.01)
*A61B 90/00* (2016.01)

(52) U.S. Cl.
CPC ...... *A61B 17/7037* (2013.01); *A61B 17/7032* (2013.01); *A61B 17/863* (2013.01); *A61B 17/864* (2013.01); *A61B 2090/037* (2016.02)

(58) Field of Classification Search
CPC ............ A61B 17/7037; A61B 17/7032; A61B 17/863; A61B 17/864
USPC ................................. 606/266–273, 308, 315
See application file for complete search history.

(56) References Cited

U.S. PATENT DOCUMENTS

| | | | | |
|---|---|---|---|---|
| 5,190,543 A | * | 3/1993 | Schlapfer | A61B 17/7032 606/256 |
| 6,074,391 A | * | 6/2000 | Metz-Stavenhagen | A61B 17/7032 606/278 |
| 6,692,500 B2 | * | 2/2004 | Reed | A61B 17/6466 606/266 |
| 7,722,651 B2 | * | 5/2010 | Kwak | A61B 17/7032 606/246 |
| 8,911,479 B2 | * | 12/2014 | Jackson | A61B 17/7035 606/278 |
| 9,655,652 B2 | * | 5/2017 | Biedermann | A61B 17/7037 |
| 9,968,378 B1 | * | 5/2018 | Johnson | A61B 17/7037 |

(Continued)

FOREIGN PATENT DOCUMENTS

EP  2 363 086 A1  9/2011
WO  2009/106733 A2  9/2009

*Primary Examiner* — Pedro Philogene
*Assistant Examiner* — David C Comstock
(74) *Attorney, Agent, or Firm* — McGlew and Tuttle, P.C.

(57) ABSTRACT

A device (1) for fixating a rod (10) on a bone with a tulip, with a pedicle screw (2) and with a tightening screw (5). The rod clamp (6) is pivotable to the tightening screw and can follow transverse motions of the rod (10). This increases the stability of the entire structure, particularly in the application in spine surgery.

33 Claims, 14 Drawing Sheets

(56) References Cited

U.S. PATENT DOCUMENTS

| | | |
|---|---|---|
| 2005/0240180 A1 | 10/2005 | Vienney et al. |
| 2006/0200131 A1 | 9/2006 | Chao et al. |
| 2008/0045955 A1 | 2/2008 | Berrevoets et al. |
| 2008/0269809 A1* | 10/2008 | Garamszegi ....... A61B 17/7037 606/305 |
| 2012/0083850 A1 | 4/2012 | Kaufman et al. |
| 2012/0150239 A1 | 6/2012 | Garamszegi |
| 2014/0188172 A1* | 7/2014 | Nichols .............. A61B 17/7004 606/278 |
| 2014/0236235 A1 | 8/2014 | Jackson et al. |

* cited by examiner

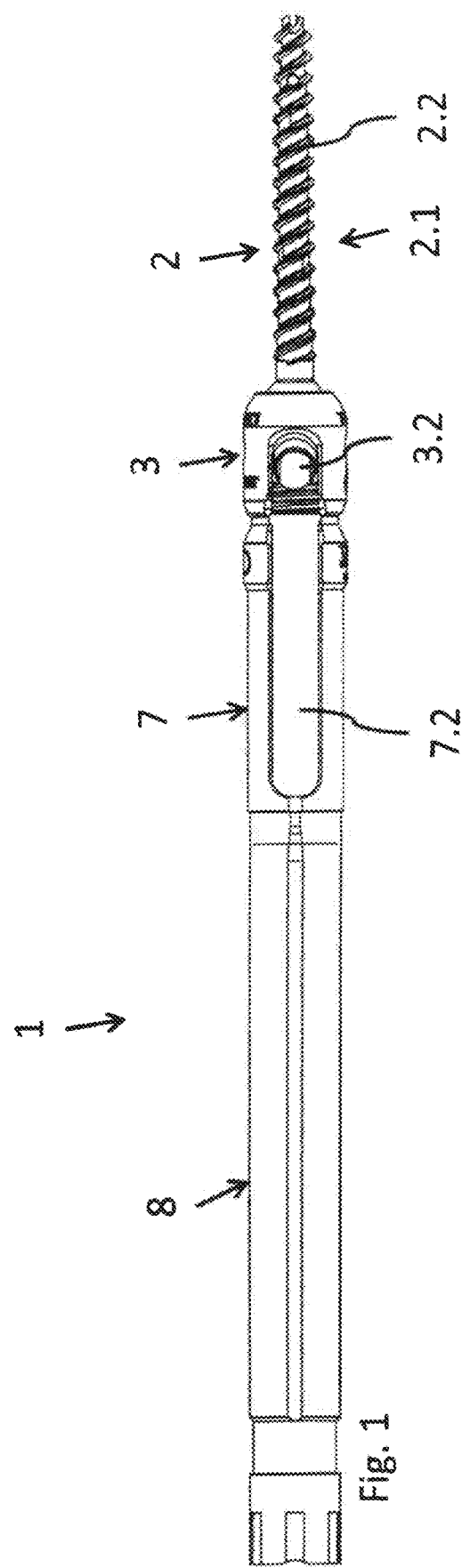
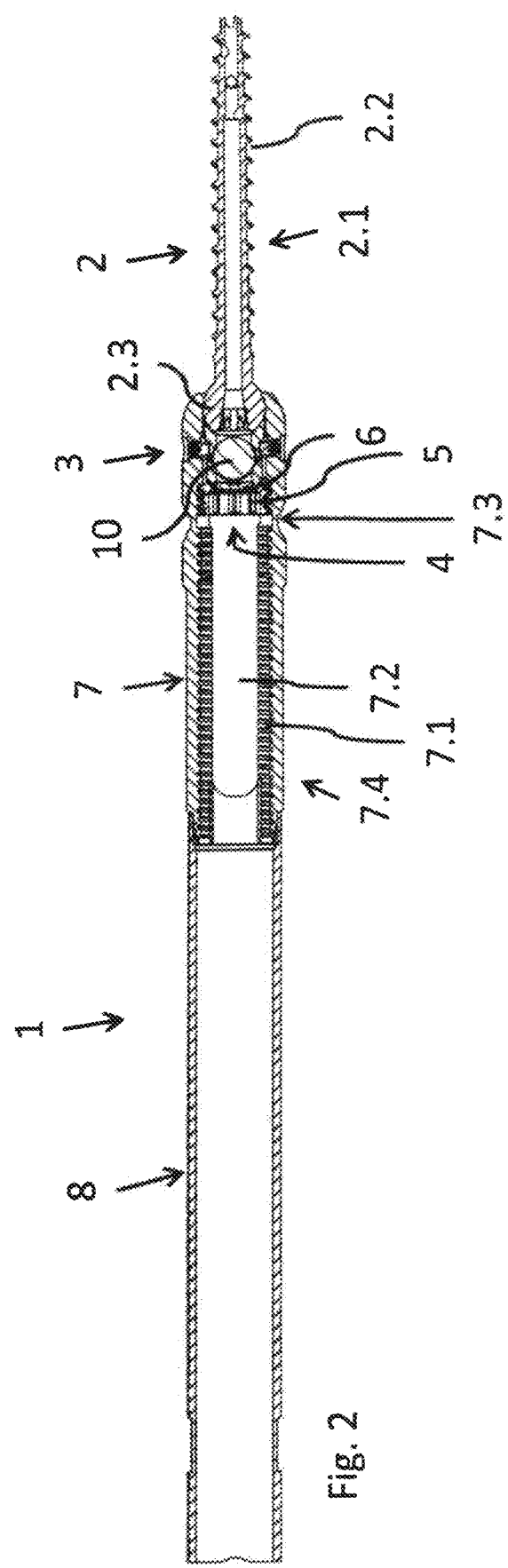
Fig. 1
Fig. 2

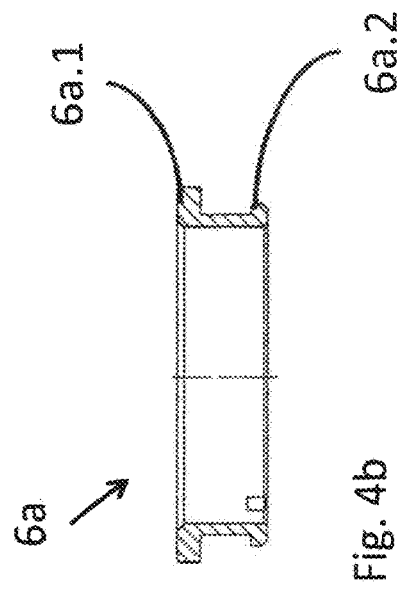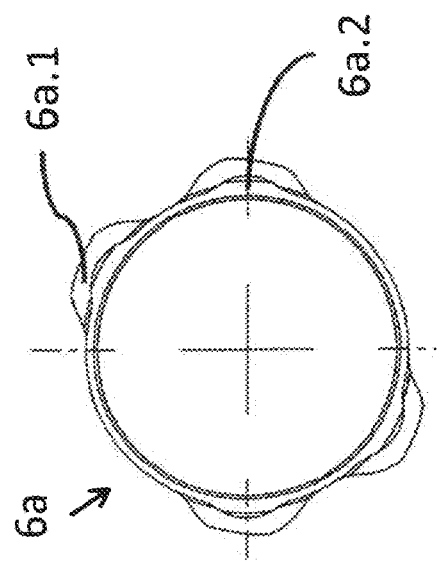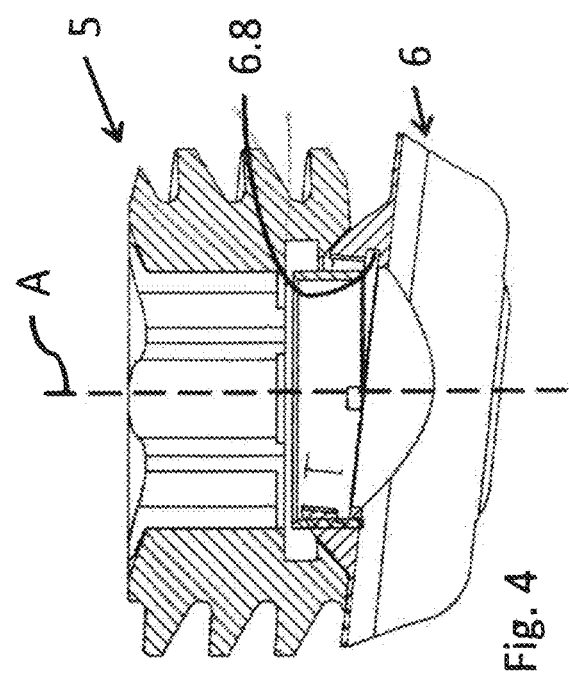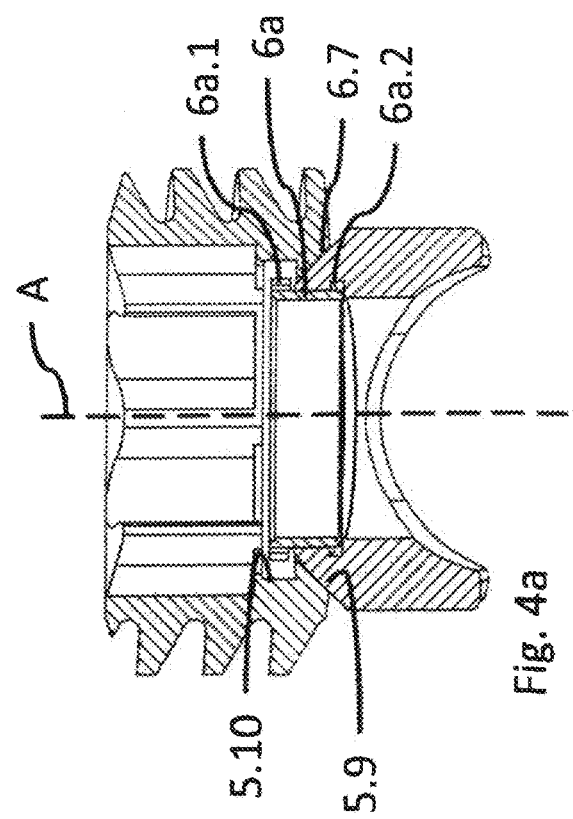

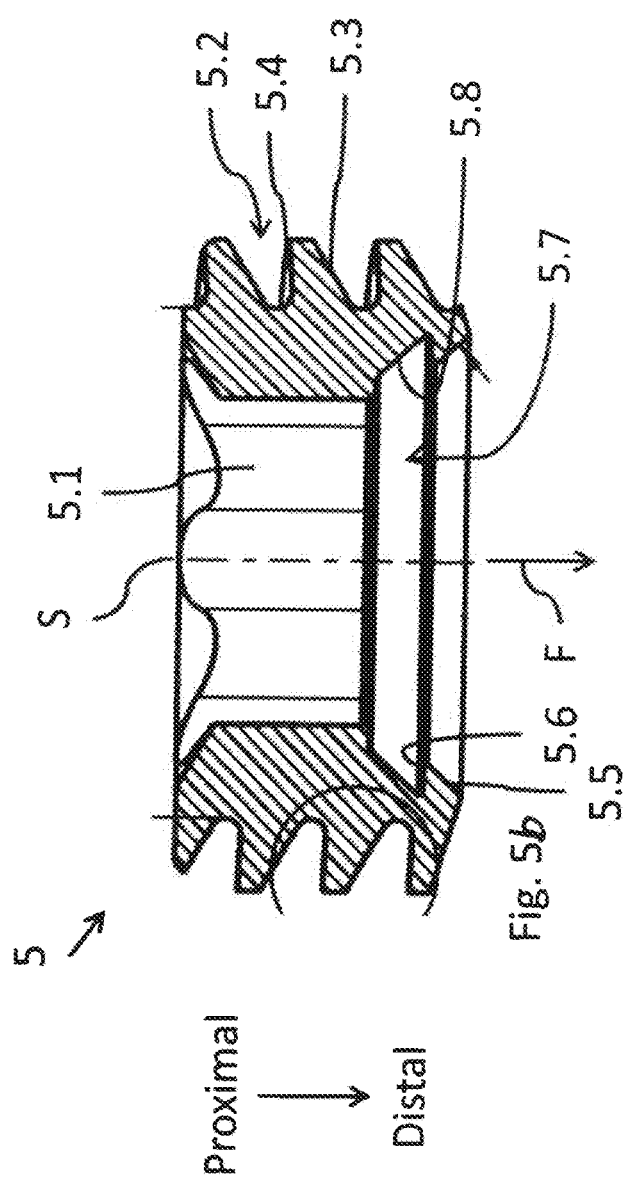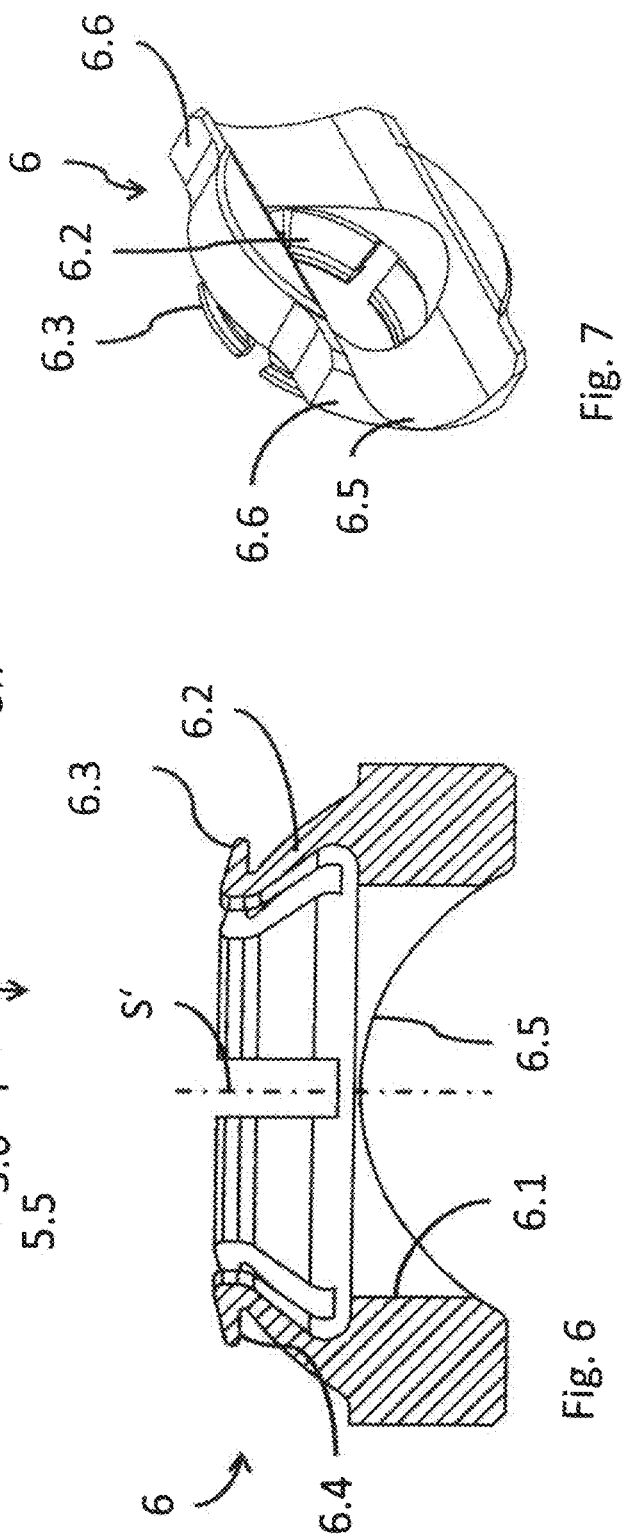

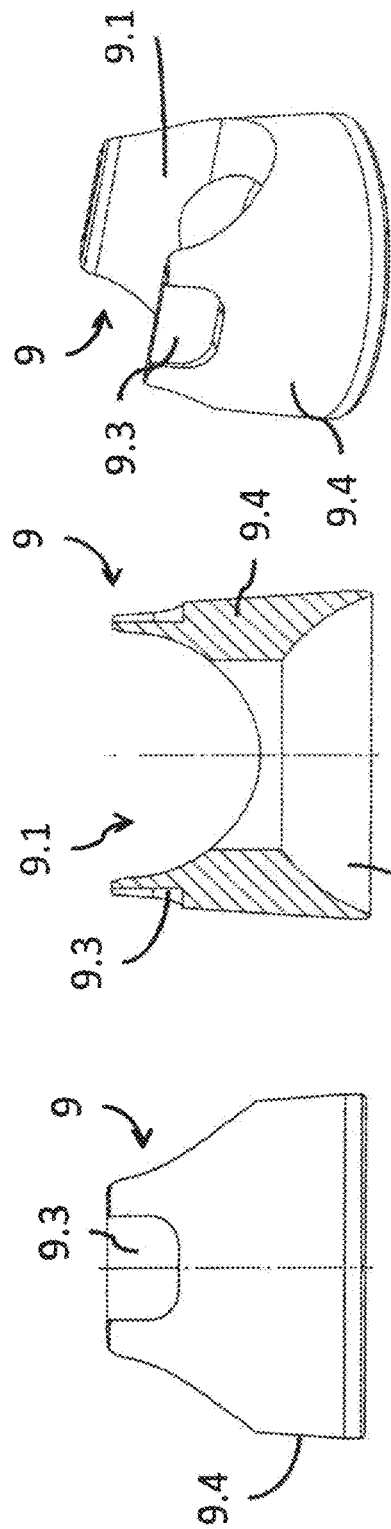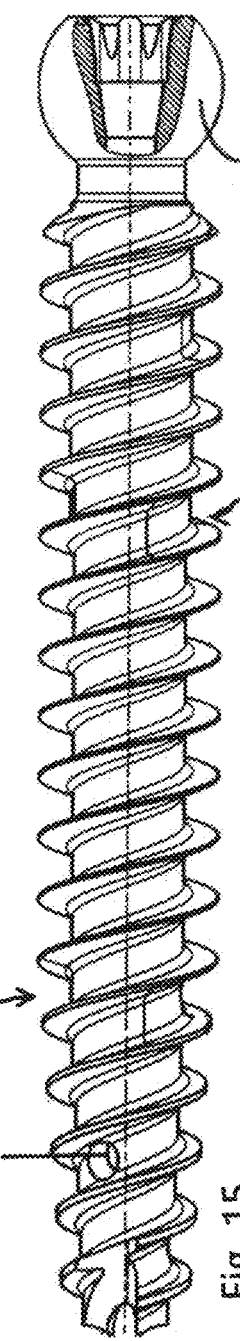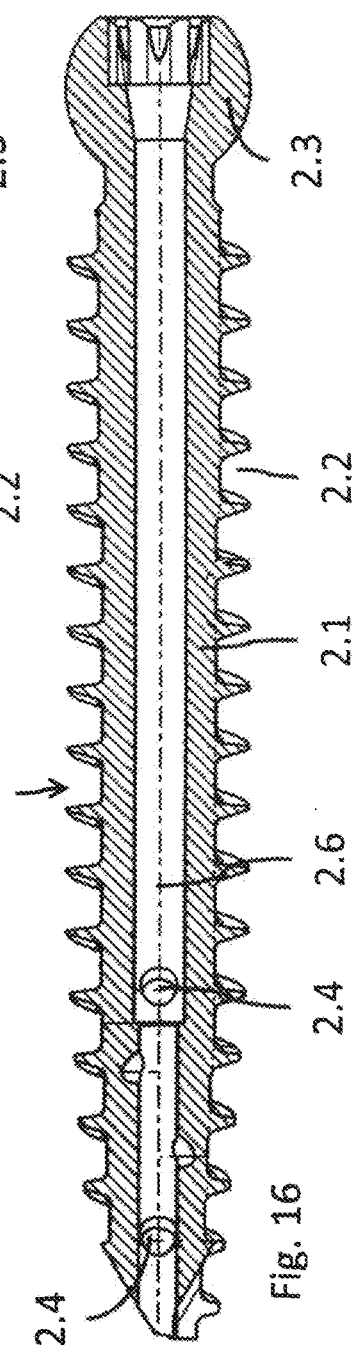

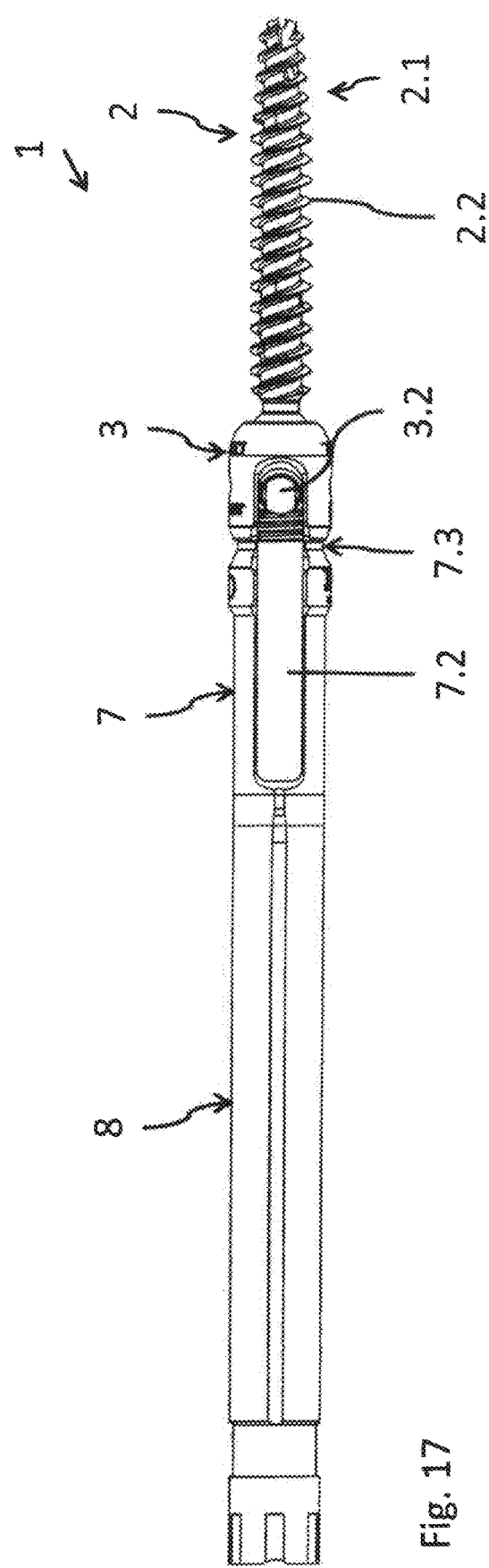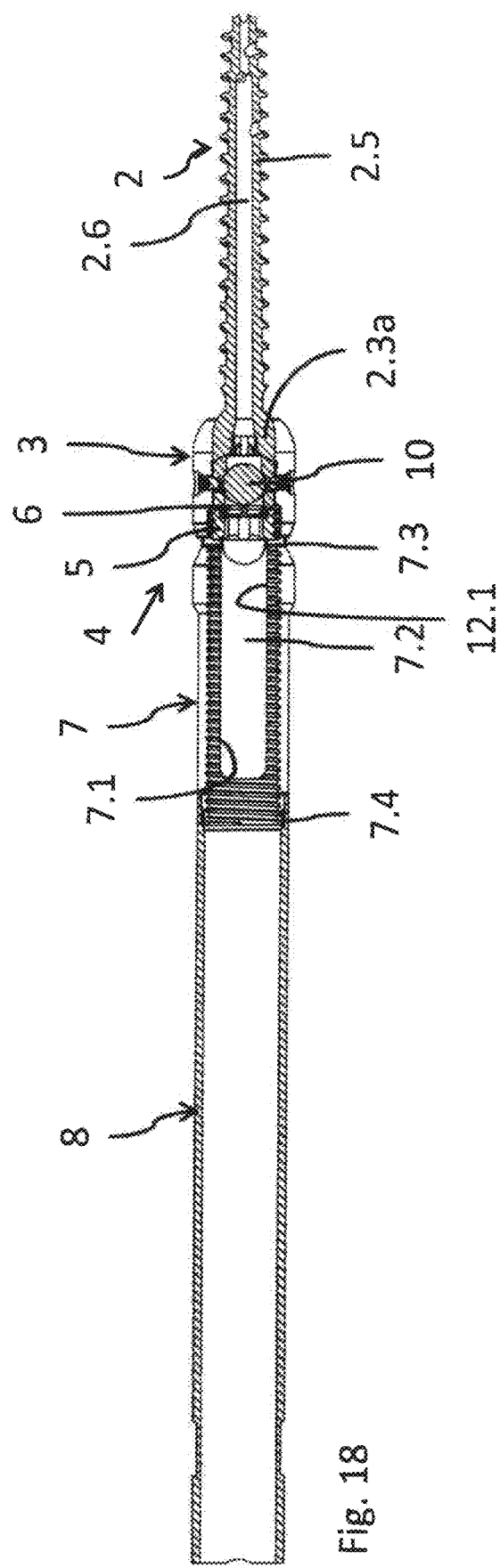
Fig. 17
Fig. 18

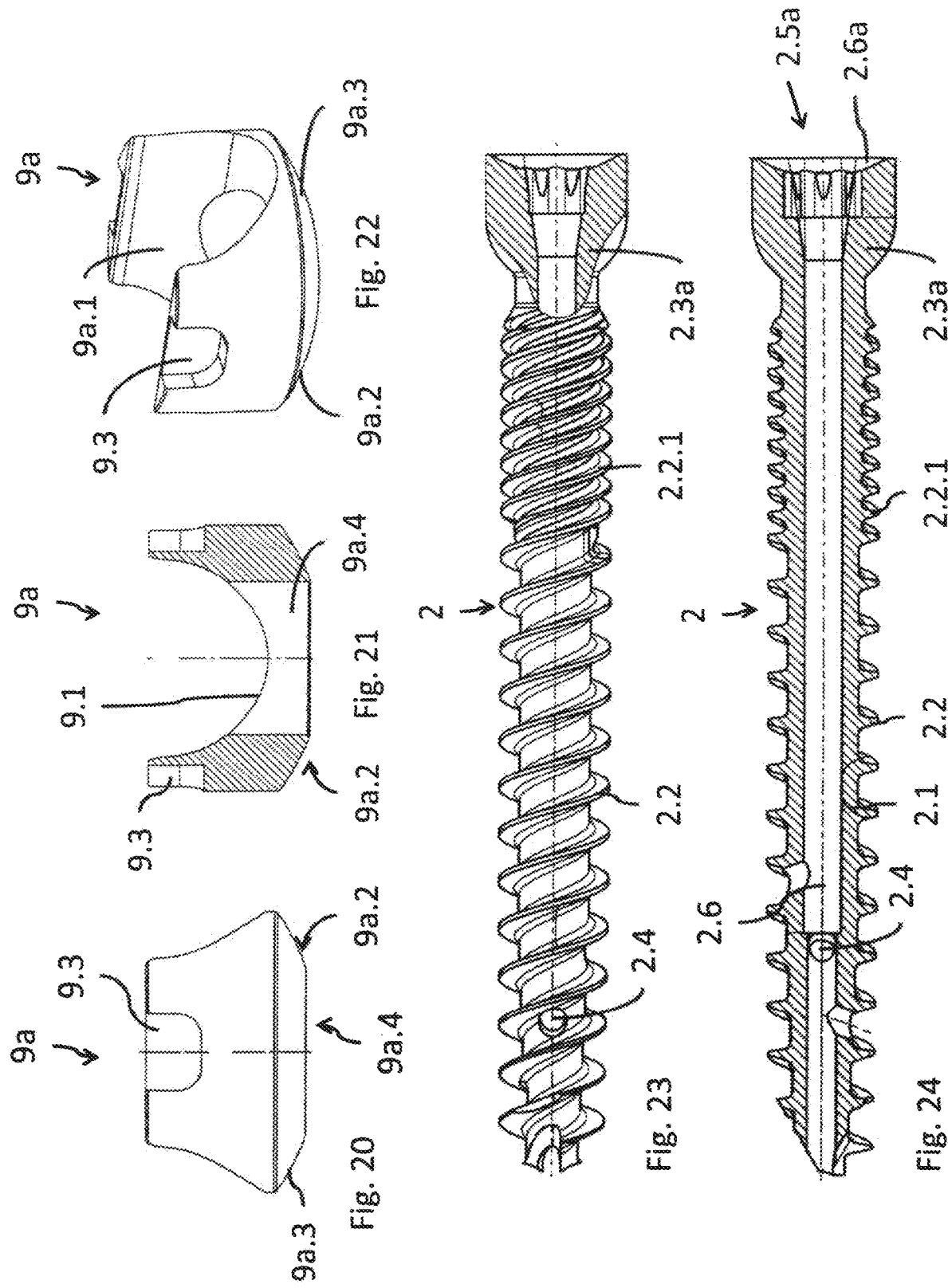

DEVICE FOR FIXATING A ROD TO A BONE

CROSS REFERENCE TO RELATED APPLICATIONS

This application is a United States National Phase Application of International Application PCT/EP2016/001479, filed Sep. 1, 2016, and claims the benefit of priority under 35 U.S.C. § 119 of German Applications 10 2015 012 909.0, filed Oct. 6, 2015, and 20 2016 004 114.3, filed Jun. 30, 2016, the entire contents of which are incorporated herein by reference.

FIELD OF THE INVENTION

The present invention pertains to a device for fixating a rod to a bone, with a tulip, a pedicle screw and a tightening screw.

BACKGROUND OF THE INVENTION

It is often necessary in case of damaged intervertebral disks but also other spinal injuries to brace two or more adjacent vertebrae by spondylodesis (fusion of vertebral bodies). Pedicle screws, which carry proximally on their rear side a tulip or rod mount, are screwed for this purpose into the vertebral bodies. A cross rod connecting a pedicle screw each and tulips in a plurality of vertebrae is braced in the tulips by means of tightening screws.

Even though it is known in this connection that pedicle screws may be configured with a spherical head or with a partially spherical head and a pressing element may be provided between the rod and the pedicle screw head, with which the tulip head and the pedicle screw can be oriented with one another monoaxially or multiaxially relative to one another at an angle, pressure screws always act directly on the (cross) rod. Although curvatures of the spine (kyphosis—chest, lordosis—lumbar region) can be taken into consideration and adapted by correspondingly bent connecting rods, undesired stresses may develop in the prior-art devices, because the tightening screw tightening the rod in the tulip head always acts at right angles, i.e., flatly in the direction of its own symmetry axis against the rod and thus it also braces this in this manner in the tulip head.

SUMMARY OF THE INVENTION

A basic object of the present invention is therefore to achieve a greater variability when bracing the rod in the tulip (rod mount) head on a device for fixating such a rod on a bone while avoiding the aforementioned drawbacks.

The above object is accomplished according to the present invention with a device of this class, which is characterized by a rod clamp pivotable to the tightening screw.

Consequently, a rod clamp, which is arranged between the tightening screw and the (cross) rod to be braced in the tulip head, and which is, moreover, also pivotable relative to the tightening screw, is provided according to the present invention in addition to the tightening screw. As a result, irregularities occurring during the spondylodesis especially over a plurality of vertebral bodies to be braced can be compensated by means of such a connecting rod.

At least a linear contact, a contact line, and hence a reliable connection and uniform transmission of forces are thus always achieved after tightening regardless of the diameter of the rod (in the predefined range of especially 5 mm to 6 mm). An only punctiform contact is ruled out.

Thus, the present invention also comprises, in particular, a system comprising at least one device according to the present invention and a (connecting) rod, in which the clamped rod is in connection between the tightening screw and the rod clamp with each of the two at least via a contact line, possibly also flatly (but not in an only punctiform manner). This applies to connecting rods with different diameters (in a limited range), preferably between 5 mm and 6 mm.

A preferred embodiment of the device according to the present invention is characterized in that the rod clamp and the tightening screw have bilateral spherical zones, which face each other and are directed obliquely to a principal axis (A), via which zones they are relatively pivotable. The spherical zones are preferably formed in the jacket area of the tightening screw and rod clamp. At the distal end of its end face, the tightening screw preferably has a ring-shaped end face extending inwardly proximally obliquely from the outer distal area in the form of a spherical zone (as a jacket of a spherical layer), and the rod clamp has a corresponding proximal end face in the form of a spherical zone.

"Proximal" designates an area of the device during its use that axially faces a surgeon or user and distally faces away from a surgeon or user and thus faces a patient or is located in the patient.

A rod clamp adapter, which connects the tightening screw and the rod clamp, is provided in a preferred variant, the rod clamp adapter being a ring part with proximally radially outwardly directed projections, which mesh with incisions in the tightening screw with a clearance, wherein especially distal, likewise radially outwardly directed projections are provided, which mesh with radial incisions of the rod clamp.

A ring groove is formed as an undercut proximally behind the end face of the tightening screw. A rod clamp for the rod to be clamped has, at its proximal end facing the tightening screw, an end face, which corresponds to the end face and likewise extends obliquely to a principal longitudinal axis. The rod clamp is likewise provided with a radial ring groove on the inner side of its jacket. Projections of the ring-shaped rod clamp adapter, which are formed radially outwardly, mesh with the ring groove in order thus to secure the rod clamp at the tightening screw against falling out.

Provisions are made in a preferred embodiment of the device according to the present invention for the tightening screw and the rod clamp to have undercuts extending behind one another, whereby a pivotable connection is ensured between the tightening screw and the rod clamp.

It is achieved hereby that the tightening screw and the rod clamp are securely connected to one another despite their relative pivoting mobility. To create the undercut, provisions are made in the embodiment according to the present invention for the undercut of the tightening screw to be formed by a an annular projection and/or for the undercut of the rod clamp to be formed on more than two elastic fingers arranged over the circumference. The number of rings and undercuts on these preferably equals four to eight. Due to the latter configuration, the tightening screw and the rod clamp, which were first prepared separately, can be connected to one another by being pushed axially against one another, with the fingers of the rod clamp yielding to behind the annular projection and their projections subsequently extending behind the annular projection of the tightening screw or the undercut thereof. Both parts are thus secured securely despite the relatively movable and especially pivotable connection.

Provisions are made in another preferred embodiment of the present invention for the tightening screw to have an inner contour tapering away from the undercut. It is thus achieved that there always is a fixed radial position between the two parts even in case of a non-axial orientation, i.e., in case of pivoting or tilting between the tightening screw and the rod clamp, because the area of the rod clamp moving towards the proximal or tapered area of the inner cone of the tightening screw is pressed by the tapered conical shape to the side and the opposite area is likewise in contact with the circumferential wall of the tightening screw in the expanded or distal area of the recess of the tightening screw correspondingly to the side.

Provisions are made according to another preferred embodiment of the device according to the present invention for the rod clamp to gave a partially circular recess on its side facing away from the tightening screw. Such a partially circular recess has a symmetry axis at right angles to the principal symmetry axis of the rod clamp and in the axially stretched arrangement thereof with the symmetry axis of the tightening screw. The partially circular recess of the rod clamp can therefore enclose the rod over a part of the circumference thereof.

Provisions are made in another preferred embodiment for the tightening screw to have an asymmetric thread, and especially a flank of the thread of the tightening screw, which flank is directed proximally to the screwdown direction, extends at an angle smaller than or equal to 5°, especially smaller than or equal to 3° or different from 0° to a radial plane to the symmetry axis of the tightening screw and/or a flank of the thread of the tightening screw, which flank is directed in the screwdown direction (distally), extends to a radial plane at an angle different from 90° to the symmetry axis of the tightening screw, preferably by 30°. The flanks are directed proximally to the perpendicular longitudinal axis of the screw.

Provisions are made according to another preferred embodiment for the tightening screw to have a plurality of—rotationally symmetrical—(non-cylindrical) depressions on its side facing away from the rod clamp. A complementarily configured screw-driving tool can thus mesh with this non-cylindrical recess of the tightening screw for screwing the screw into the tulip of the device.

Another embodiment of the present invention is characterized by a pressing element mounted in the tulip opposite the rod clamp, wherein said pressing element is especially mounted tiltably in the tulip. Provisions are furthermore made in this connection for the diameter of the pressing element to be reduced on at least one of its end faces compared to the internal diameter of the tulip, so that the pressing element is tiltable within the tulip. The pressing element of the tulip tapers from its distal end face to its proximal end face, so that there is a radial clearance between the inner wall of the tulip and the outer wall of the pressing element or the inner wall of the tulip expands from the level of the proximal end face to the level of the distal end face of the pressing element while a radial clearance is guaranteed between the pressing element and the tulip at the level of the distal end face of the pressing element.

The pressing element, which is located distally opposite the rod clamp and clamps the rod between this rod clamp and itself, is configured and/or mounted in connection or in relation to the interior space of the enclosing tulip such that the pressing element assumes the orientation of the clamped rod, which is made possible by the clamping device, it likewise makes it possible and does not prevent it.

A fixating device according to the present invention has a pedicle screw, a pressing element and a tulip. It further has a clamping device with a tightening screw and with a rod clamp. All these parts are cannulated, i.e., they have an axially extending central cavity.

The tulip holds the pedicle screw and is used to mount a rod after the pedicle screw has been screwed into a bone. The tulip is consequently a rod mount and is also designated as such.

The tulip is connected to a tulip extension proximally via a predetermined breaking point. The tulip and the tulip extension have an internal thread extending over both and diametrically opposite elongated holes in the wall of both.

The pedicle screw has a pedicle screw shaft with a self-tapping pedicle thread and, at the proximal end, a pedicle screw head, which is enclosed by the tulip. A pressing element for the rod is arranged as an abutment in the distal area of the tulip.

Provisions are made in a preferred embodiment for the screw shaft of the pedicle screw to have a double thread, wherein especially a proximal area of the screw shaft is configured as a quadruple thread, preferably over a length of one fourth of the pedicle screw shaft. Better hold of the screw in the bone is achieved hereby. A double thread has two screw threads. A double thread has two threads. These are wound in one another.

The transition from the screw thread projection or indentation to the screw shaft is rounded with a finite radius of curvature of the transition. The stability of the screw is increased and the screw flanks are prevented from breaking off hereby.

The pedicle screw shaft is provided with openings around a jacket to its inner lumen. Especially pasty compounds, such as bone cement, can be introduced through a lumen of the screw and openings. It is essential in this connection that the openings are present in the distal area of the screw, so that they will be located after insertion of the screw within the vertebral body (and not in the bone area), so that cement can then be introduced through these into the interior of the vertebral body for fixation.

An external thread of the tightening screw is coordinated with an internal thread of the tulip. A rod inserted into the tulip is clamped between the rod clamp, which encloses it from the proximal side and on which the tightening screw acts, and the distally acting pressing element, by which parts the rod can be clamped with angles equal to or also different from 90°, especially in relation to the device axis.

Preferred concrete embodiments of individual components are mentioned below. A plurality of non-cylindrical depressions are provided at the proximal end of the tightening screw for positive-locking meshing with a screw-driving tool for transmitting a torque to the tightening screw. The outer side of the tightening screw is provided with an asymmetric tightening screw thread, especially in the form of a special buttress thread.

Proximally behind its distal end face, the tightening screw has a ring projection in the form of an inner cone, which extends proximally from the distal end face, and which is adjoined via an undercut proximally by an inner cone tapering the lumen of the tightening screw in the proximal direction, which inner cone has radially a larger diameter compared to the depression at the distal end area of the depression of the tightening screw.

The rod clamp has a number of elastic fingers arranged next to each other in the circumferential direction and directed in the proximal direction and radially inwardly with radially outwardly pointing bosses, which interact with the undercuts of the tightening screw by the bosses snapping with their undercuts into the undercut of the tightening screw, which latter undercut is formed by the ring projection.

The distal end face of the rod clamp has a partially cylindrical clamping recess for receiving the cross rod.

Based on the dimensioning of the inner cone of the tightening screw, a tilting motion of the rod clamp in the tightening screw is possible. Due to the configuration of the proximally tapering inner cone, the bosses of the rod clamp are in contact with the inner wall of the inner cone in the tilted position of the rod clamp as well. The radial fixation of the rod clamp 6 is guaranteed in this manner in the axially oriented position and in the tilted position.

A multiaxial pressing element has, on its proximal side, a partially cylindrical recess for partially enclosing and receiving the rod, while another hemispherical or dome-shaped recess on the distal end face of the pressing element is provided in order to grasp a spherical screw head of the pedicle screw.

The pressing element, which is a distal pressing element relative to the rod, has a jacket tapering from its distal end to the proximal end, so that a gap is formed between this pressing element and the inner wall of the tulip. As a result, tilting of the pressing element is possible within the tulip in relation to an axially oriented central position.

The partially cylindrical recess has such a radius of curvature that rods with different diameters, e.g., between 5 mm and 6 mm, can be used.

On its outer side, the pressing element has pressing surfaces for cross bolts that can be screwed in radially from the outside through the tulip to fix the pressing element within the tulip.

The multiaxial pedicle screw has a spherical pedicle screw head, which is unlimitedly pivotable in all directions in the spherical recess at the distal area of the multiaxial pressing element. The screw head and hence the pedicle screw 2 is held securely in the tulip, because the latter has a narrowed opening compared to the diameter of the screw head at its distal end.

A monoaxial pressing element has a flat frustoconical distal end face facing the screw head of the pedicle screw with a conical ring-shaped circumferential edge, which encloses a central opening.

The pressing element and the pedicle screw are rotatable relative to one another in the monoaxial orientation, but they always remain oriented monoaxially along an axis that is identical to the axis of the tulip and of the tightening screw screwed into same.

The inner wall of the tulip has a shoulder and, proximally behind this, an expansion, which tapers monoaxially in the proximal direction. The screw head extends proximally to this shoulder in the tulip. The—monoaxial—pressing element begins distally only there and has at its distal end a smaller diameter than the expansion of the tulip, so that a certain lateral clearance is present there and the monoaxial pressing element can thus easily be tilted in the tulip in order not to thus hinder an eccentric orientation of the rod, which is permitted by the clamping device, but rather to assume it and to make it possible.

At its proximal end, a monoaxial pedicle screw has a—monoaxial—pedicle screw head, which can be pivoted correspondingly. The screw head has a cylindrical jacket and a flat proximal end face-side depression with a likewise conical ring-shaped edge adapted to the circumferential edge of the pressing element.

Tilted arrangements of the connecting rod can be adjusted by the clamping device with the rod clamp by a corresponding pivoting motion of the rod clamp and of the pressure element, which at least considerably reduces stresses on the fixating device, on the one hand, and the stress of the patient, on the other hand; the stability of the fixating device, especially the long-term stability thereof, are substantially increased hereby. The stability of the structure is thus improved due to the variability of the orientation of the cross rod in the device.

Further advantages and features of the present invention appear from the claims and from the following description, in which exemplary embodiments are explained in detail with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a lateral view showing a fixating device according to the present invention in a multiaxial configuration;

FIG. 2 is a longitudinal sectional view of the device according to FIG. 1;

FIG. 4 is a longitudinal sectional view through the clamping device according to the first embodiment with a rod clamp sloped to the tightening screw;

FIG. 4a is a longitudinal sectional view of the embodiment of FIG. 4 in a longitudinal section offset by 90° about the longitudinal axis A of the device;

FIG. 4b is a longitudinal sectional view of a rod clamp adapter;

FIG. 4c is a distal end face view of the rod clamp adapter;

FIG. 5 is a longitudinal sectional view of a fixating device in a modified second configuration especially of the clamping device, similar to that according to FIGS. 1 through 3a;

FIG. 5b is a longitudinal sectional view of a tightening screw of the second embodiment according to FIGS. 5, 5a;

FIG. 6 is a longitudinal sectional view of a rod clamp of the second embodiment according to FIGS. 5, 5a;

FIG. 7 is a perspective view of the rod clamp according to FIG. 6;

FIG. 12 is a lateral view of a multiaxial pressing element;

FIG. 13 is a sectional view of the pressing element according to FIG. 12 and rotated axially by 90°;

FIG. 14 is a perspective view of the pressing element according to FIGS. 12 and 13;

FIG. 15 is a lateral partially sectional view of a multiaxial pedicle screw;

FIG. 16 is a sectional view of a pedicle screw according to FIG. 15;

FIG. 17 is a lateral view of another embodiment of a fixating device;

FIG. 18 is a sectional view of the fixating device according to FIG. 17;

FIG. 20 is a lateral view of a monoaxial pressing element;

FIG. 21 is a sectional view of the pressing element according to FIG. 20, rotated axially by 90°;

FIG. 22 is a perspective view of the pressing element according to FIGS. 20 and 21;

FIG. 23 is a lateral view partially sectional view of a monoaxial pedicle screw with a partial view of a quadruple thread; and FIG. 24 is a longitudinal sectional view of the pedicle screw according to FIG. 23.

DESCRIPTION OF THE PREFERRED EMBODIMENTS

Figure 2A:
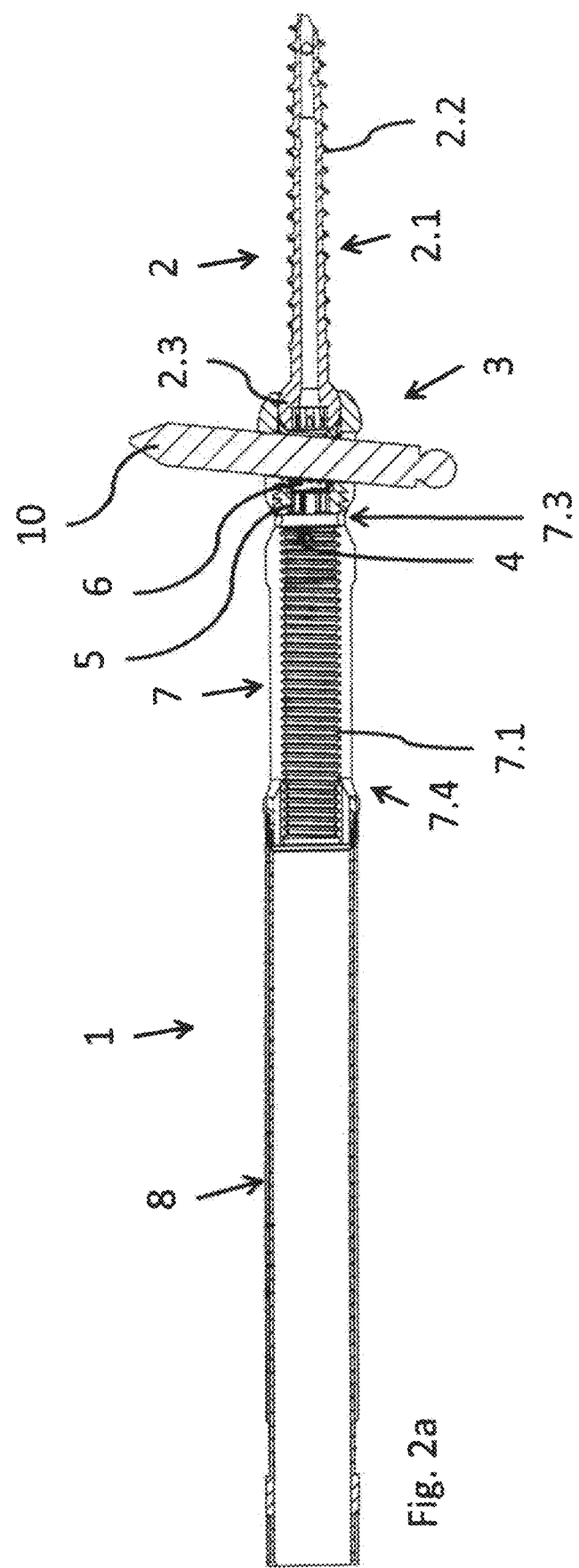
FIG. 2a is a longitudinal sectional view of the device according to FIGS. 1 and 2 at 90° to that in FIG. 2 and with a rod inserted.

Referring to the drawings, FIG. 1 shows a fixating device 1 with a—multiaxial—pedicle screw 2 and with a tulip 3. The device 1 has a principal axis A in its longitudinal direction. It further has a clamping device 4 with a tightening screw 5 and with a rod clamp 6, which are shown in a sectional view in FIG. 2 and especially also in FIG. 3. All these parts are cannulated, i.e., they have an axially extending central cavity.

The word "proximal" hereinafter designates an area of the device 1 during its use that faces—axially—a surgeon or user and faces distally away from this user and thus faces a patient or is located in same.

The tulip (rod mount) 3 holds the pedicle screw 2 and is used, after the latter has been screwed into a bone, especially into a vertebra, to mount a rod 10 (FIGS. 2, 3), which extends especially in the direction of the spine or also of a long bone or in the direction of a flat bone and which can also be held by additional tulips with pedicle screws at another bone/vertebra or at another location, e.g., of a long bone and can thus fixate the bone/vertebra. The tulip 3 is consequently a rod mount and is also designated as such.

At its proximal end, the tulip 3 is first connected via a predetermined breaking point 7.3 to a tulip extension 7. As a transition area between the tulip 3 and the tulip extension 7, the predetermined breaking point 7.3 has a radially reduced cross section or a reduced wall thickness. At a proximal end 7.4 of the tulip extension 7, the latter has an external thread (not shown) for connection to an extension shaft 8 having a corresponding internal thread.

The tulip 3 and the tulip extension 7 are cannulated, just like the extension shaft 8. The tulip 3 and the tulip extension 7 have an internal thread 3.1, 7.1 extending over both. Further, diametrically opposite elongated holes 3.2, 7.2, which extend axially over the largest part of the tulip extension 7 and over about half of the tulip 3, extend in the distal area of the tulip extension 7 and in the proximal area of the tulip 3 in the walls of both.

The pedicle screw 2 has a pedicle screw shaft 2.1 with a self-tapping pedicle thread 2.2. A pedicle screw head 2.3, which is enclosed by the tulip 3, is formed at the proximal end of the pedicle screw 2 (FIGS. 1 through 3).

A pressing element 9, whose mode of action will be described farther below, is arranged in the distal area of the tulip 3, into which the pedicle screw head 2.3 is screwed.

The pedicle screw 2 shown has a double thread, i.e., two screw threads S1, S2 (FIG. 15). The pedicle screw 2 may also have a single thread or multiple threads (differing from a double thread).

The pedicle screw shaft 2.1 is provided with openings 2.4 in a jacket 2.5 to an inner lumen 2.6 of the pedicle screw 2. The lumen 2.6 passes axially through the entire pedicle screw 2. Liquids and/or especially pasty compounds, such as cleaning liquids or bone cement, may be introduced through the lumen 2.6 and the openings 2.4.

An external thread 5.2 of a tightening screw 5 is coordinated with an internal thread 3.1 of the tulip 3 (described in more detail below).

Figure 3:
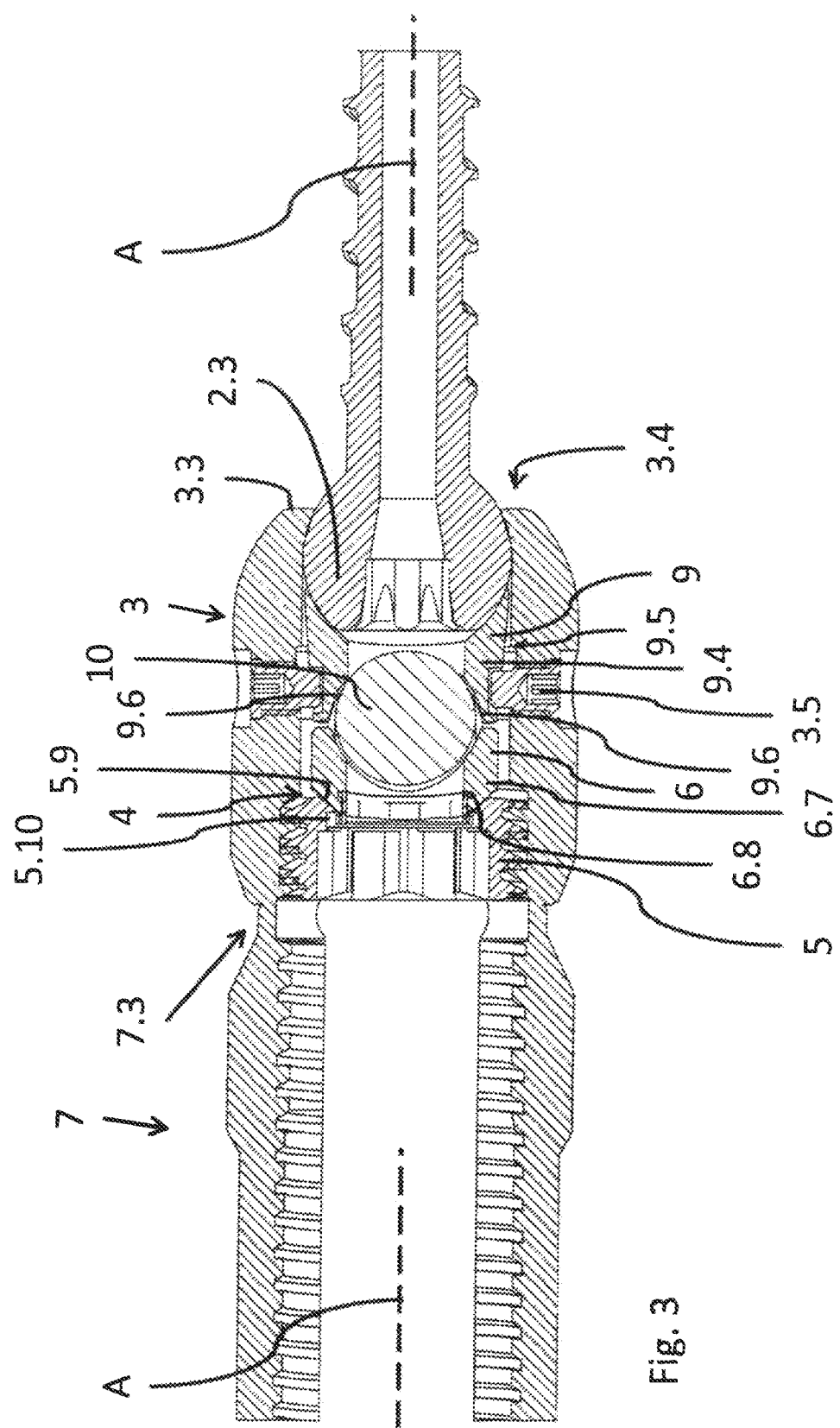
FIG. 3 is an enlarged partial longitudinal sectional view of the fixating device according to FIGS. 1 through 2a with a first configuration of a clamping device.

A rod 10, which is clamped in the tulip 3 and which is clamped between the rod clamp 6, on which clamp the tightening screw 5 acts and which encloses it from the proximal side, and the distally acting pressing element 9, is seen (in a sectional view) in FIG. 2 (and also in connection with FIGS. 2a through 4a). The clamping of the rod 10 will be described below.

Figure 3A:
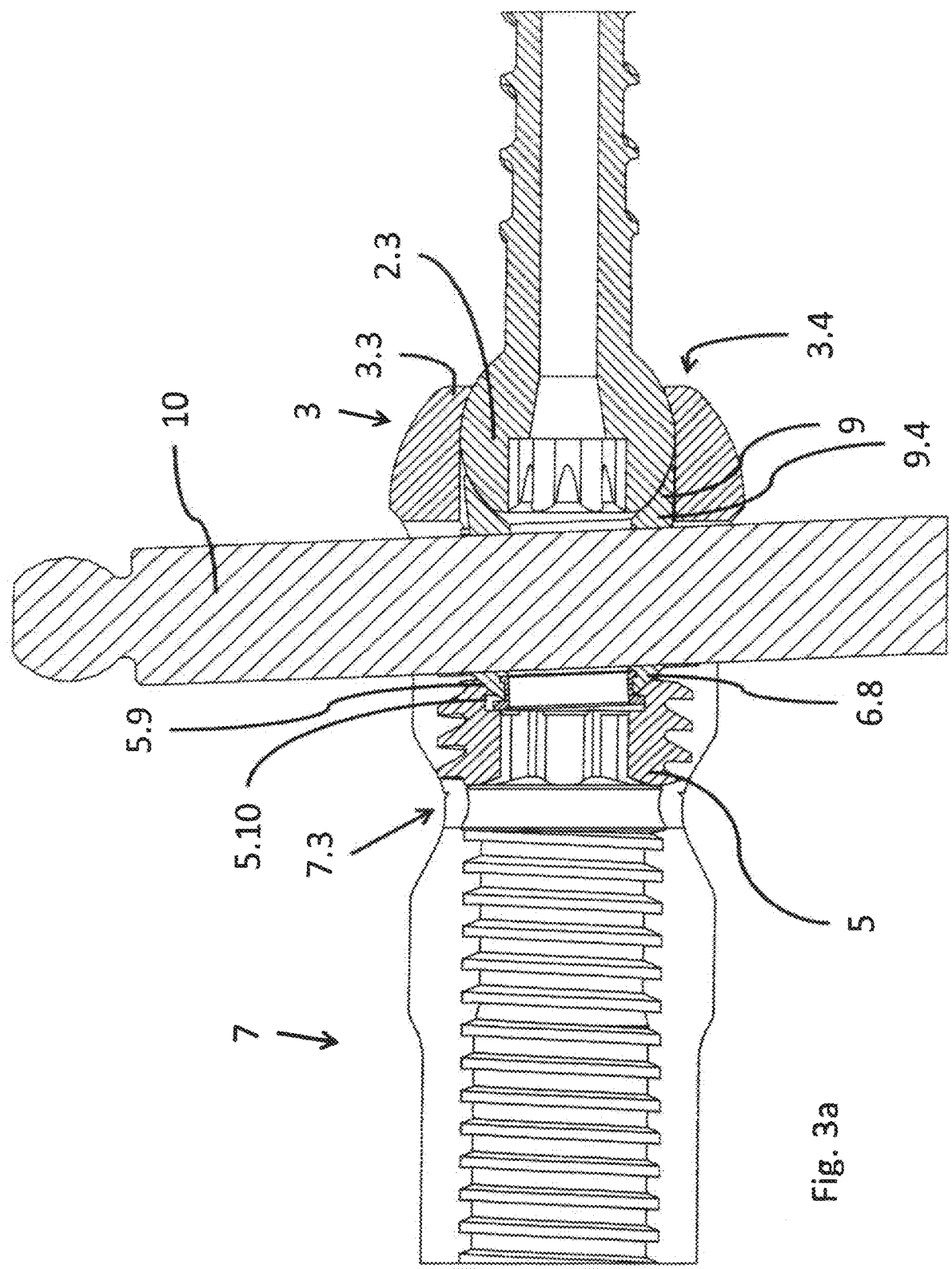
FIG. 3a is the fixating device according to FIGS. 1 through 3 in an enlarged partial longitudinal section at 90° relative to the section shown in FIG. 3.

FIG. 3a shows a section through the device 1 according to the present invention with a rod 10 with an angle different from 90° in relation to the axis of the device to show how such an orientation is made possible by the embodiment of the individual components, which will be described below.

The tightening screw 5 (FIGS. 3, 3a) has an axial symmetry axis, which coincides with the principal axis A. A plurality of non-cylindrical depressions 5.1, which offer a positive-locking meshing for a screw-driving tool (screwdriver, not shown) for the transmission of a torque to the tightening screw 5, are provided at the proximal end of the tightening screw 5. The depression 5.1 may be configured as a tetragon or polygon, especially also as a Torx profile.

The outer side of the tightening screw 5 is provided with the asymmetrical tightening screw thread 5.2, and the screw-down direction F is directed downward. The tightening screw thread 5.2 is configured in FIG. 5 as a buttress thread. Other types of thread, especially other types of asymmetric thread, are likewise possible.

The flanks 5.3, 5.4 are sloped in the same direction from the inside to the outside in the proximal direction relative to radial planes (which are at right angles to the axis), in the tightening screw thread 5.2 in the form of a special buttress thread, the distally directed flank 5.3 of a tooth body being sloped here by 30° and the proximally directed flank 5.4 of the screw thread by 3°, so that the flank angle (between two flanks) equals 27°. Such a buttress thread can be subjected to high loads in case of forces acting opposite the screw-down direction.

At its distal end, the tightening screw 5 correspondingly has in this first embodiment, corresponding especially to FIG. 3, a ring-shaped end face 5.9 generally extending distally from the outside and proximally obliquely on the inside relative to the axis A in the form of a spherical zone (as a jacket of a spherical layer). A radial ring groove 5.10 is formed as an undercut proximally behind this. A rod clamp 6 for the rod 10 to be clamped has, at its proximal end facing the tightening screw 5, an end face 6.7, which likewise extends obliquely to the axis A and corresponds to the end face 5.9. The rod clamp 6 is also provided with a radial ring groove 6.8 on the inner side of its jacket. Radially outwardly directed projections 6a.1 and 6a.2 of a ring-shaped rod clamp adapter, whose number equals four here, and which are not arranged uniformly over the circumference, mesh with the ring grooves 5.10, 6.8, in order thus to secure the rod clamp 6 at the tightening screw 5 from falling out. The rod clamp adapter is preferably welded to the rod clamp 6.

Figure 5:
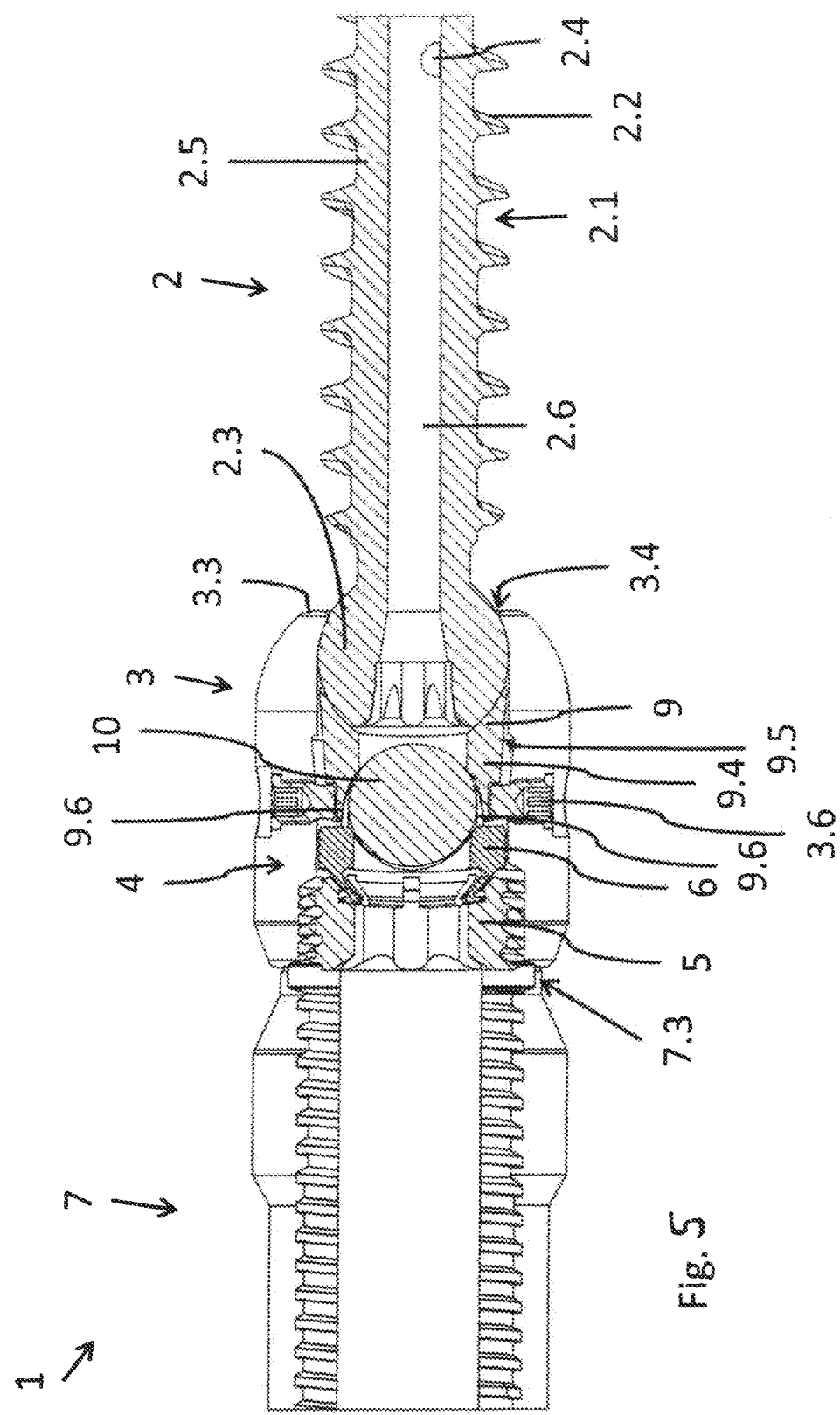
Figure 5A:
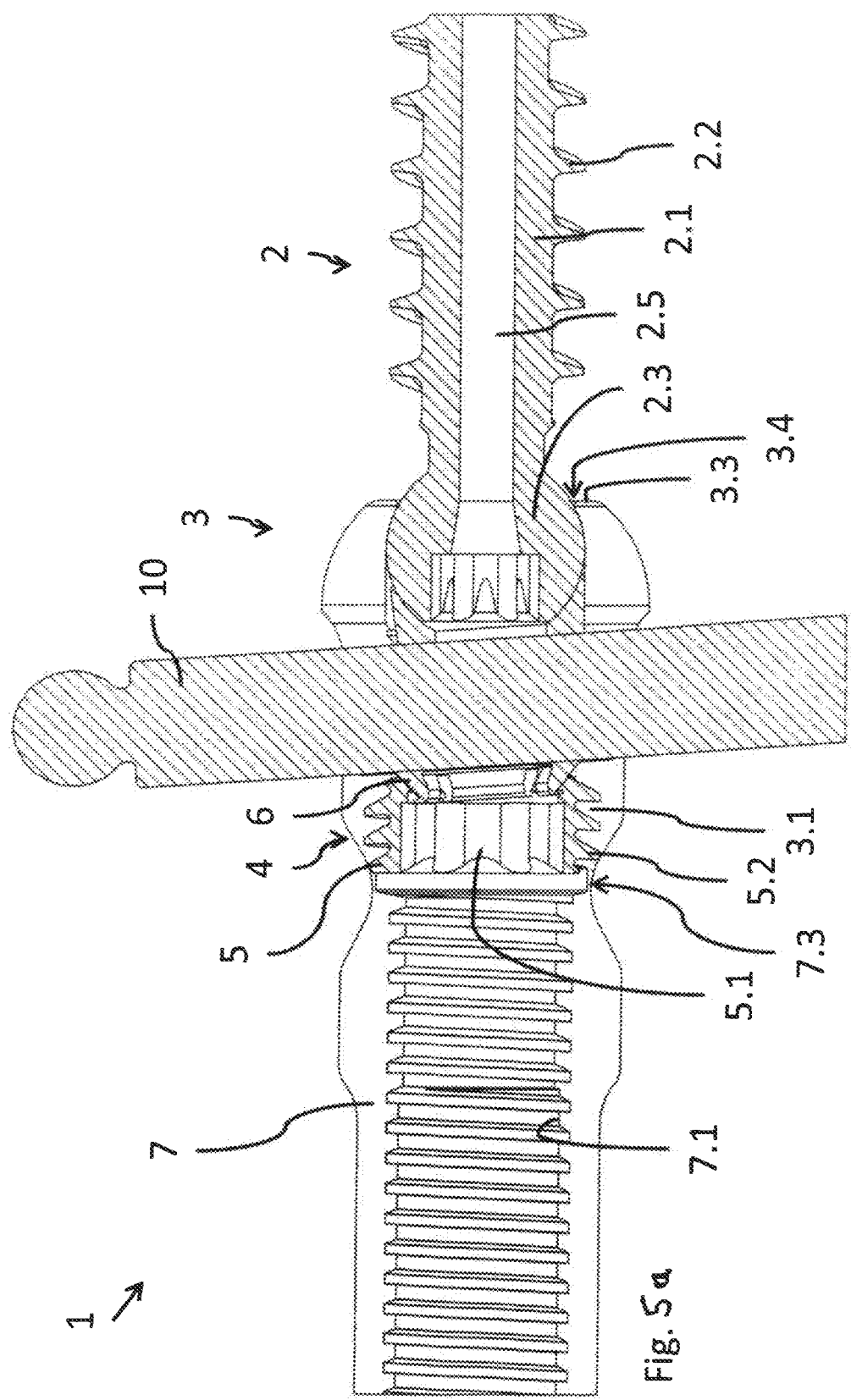
FIG. 5a is a longitudinal sectional view through the device according to FIG. 5 corresponding to FIG. 2a with a cross rod directed at an angle different from 90° to the longitudinal axis of the device in a longitudinal section offset by 90° relative to the section according to FIG. 5.

FIG. 5 shows a tightening screw 5 according to the second embodiment of the clamping device 4 in an axial longitudinal section. Insofar as it is identical to the tightening screw described with reference to FIGS. 3, 3a, reference is made to the description given there.

The tightening screw 5 has, proximally behind its distal end face, a ring projection in the form of an inner cone, which extends proximally from the distal end face and is adjoined via an undercut 5.6 proximally by a lumen 5.7 of the tightening screw 5 having an inner cone 5.8 tapering in the proximal direction, which ends axially at the distal end area of the depression 5.1 of the tightening screw 5 and has radially a larger diameter there than the depression 5.1.

The rod clamp 6 likewise has a ring-shaped configuration with a lumen (FIG. 6) and is provided on its distal end face with a hole 6.1, which extends axially over about half of the height of the rod clamp 6 and has radially a constant cross section. At the proximal end of the hole 6.1, the rod clamp 6 has a number of elastic fingers 6.2, which are arranged next to one another in the circumferential direction and are directed radially inwardly, and which has at their end area radially outwardly pointing bosses 6.3, which form undercuts 6.4. The axial symmetry axis S' of the rod clamp 6 coincides with the symmetry axis S of the tightening screw 5. The interaction of the tightening screw 5 with the rod clamp 6 will be discussed below.

The distal end face of the rod clamp 6 has a partially cylindrical clamping recess 6.5 for receiving the cross rod 10 (FIG. 7). The rod clamp 6 has attachments 6.6 on both sides in the direction of one symmetry axis of the partially cylindrical recess 6.5.

Figure 9:
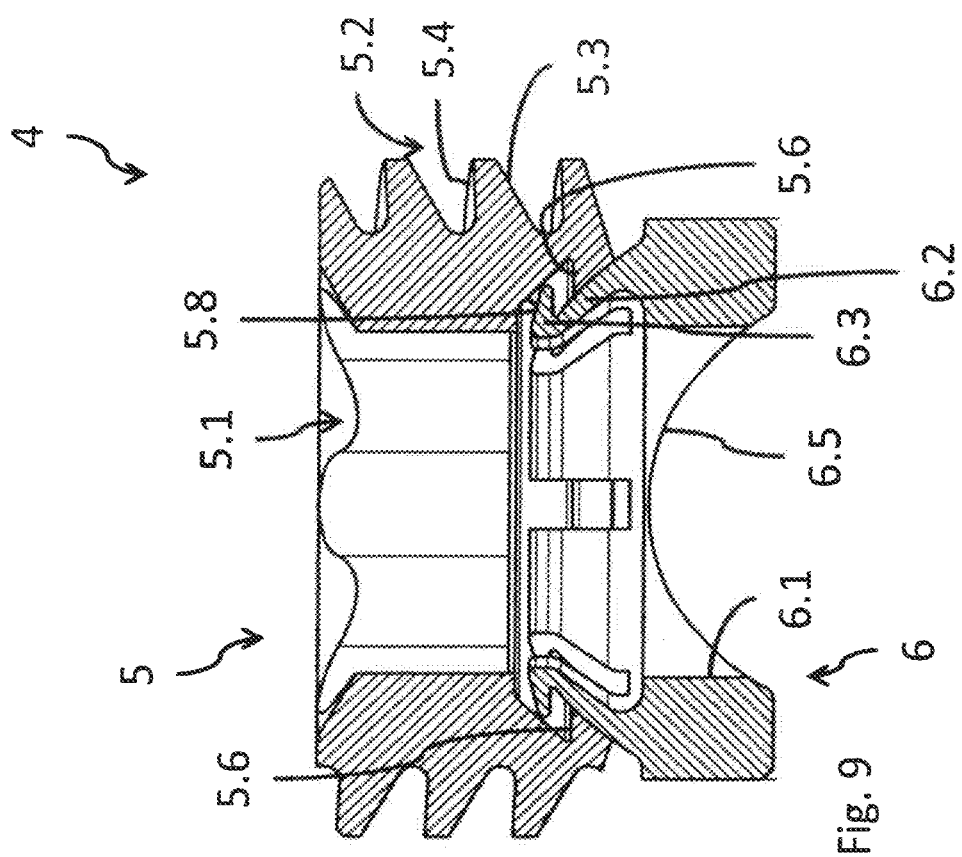
FIG. 9 is a longitudinal sectional view of the clamping device according to FIG. 8 in a sectional view rotated axially by 90°.
Figure 8:
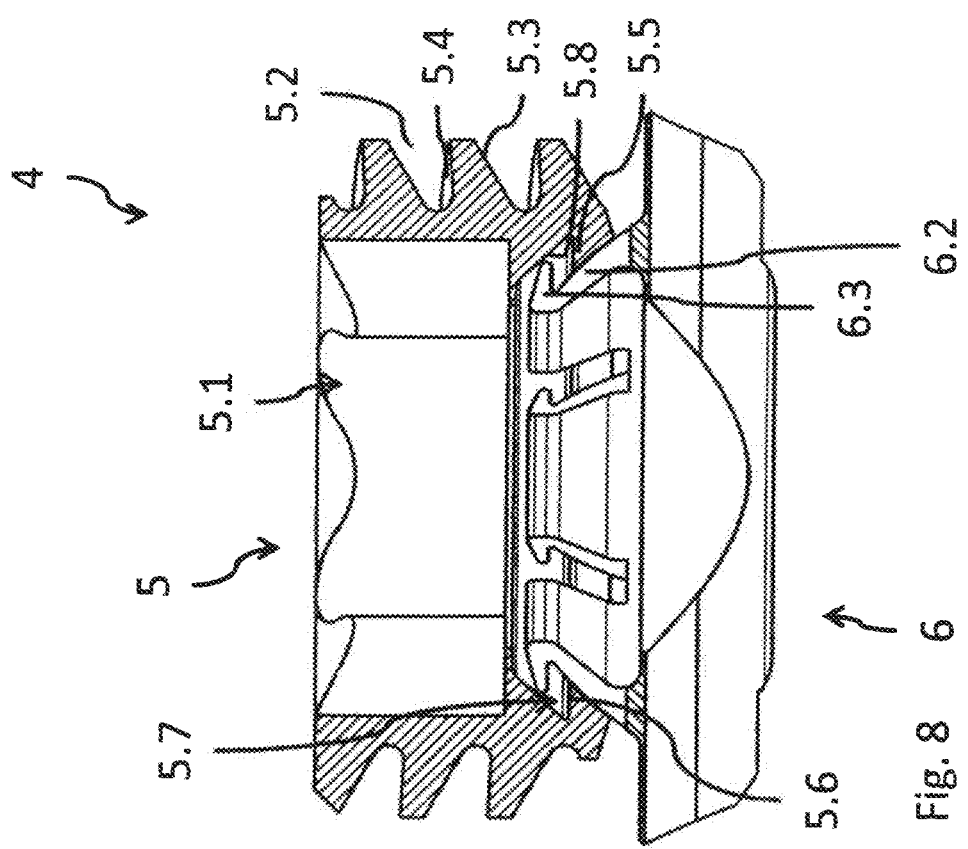
FIG. 8 is a schematic sectional view of a clamping device of the second embodiment.

FIG. 8 shows the clamping device 4 with the tightening screw 5 and the rod clamp 6 assembled. The tightening screw 5 and the rod clamp are moved for this axially towards one another, so that the bosses 6.3 of the rod clamp 6 first come into contact with the conical ring projection 5.5 of the tightening screw 5. The fingers 6.2 are pressed radially inwardly by the contact flank of the ring projection 5.5 during the further axial motion, as a result of which an additional relative axial motion is allowed. If the bosses 6.3 of the fingers 6.2 reach the undercut 5.6 beyond the ring projection 5.5, the bosses 6.3 with undercuts 6.4 snap into the undercut 5.6 of the tightening screw 5, which undercut 5.6 is formed by the ring projection 5.5. As a result, the tightening screw 5 is connected securely to the rod clamp 6. FIGS. 8 and 9 show sectional views rotated by 90° in relation to one another.

Figure 11:
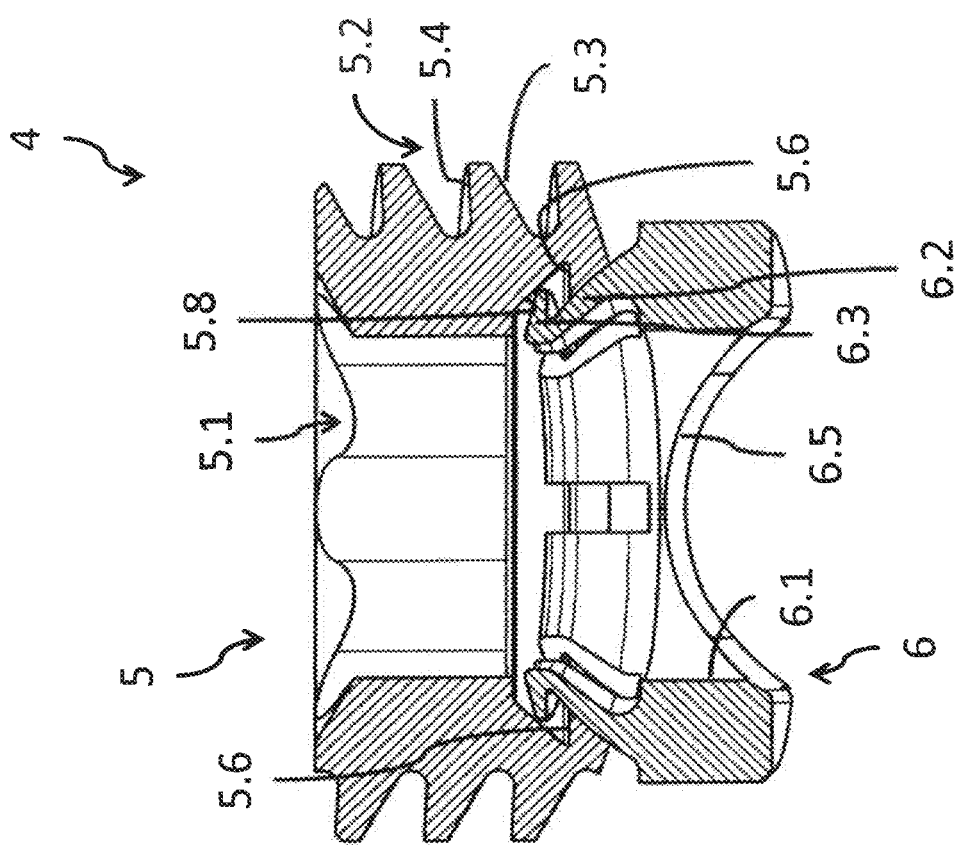
FIG. 11 is a longitudinal sectional view of the clamping device according to FIG. 10 in a sectional view and rotated axially by 90°.
Figure 10:
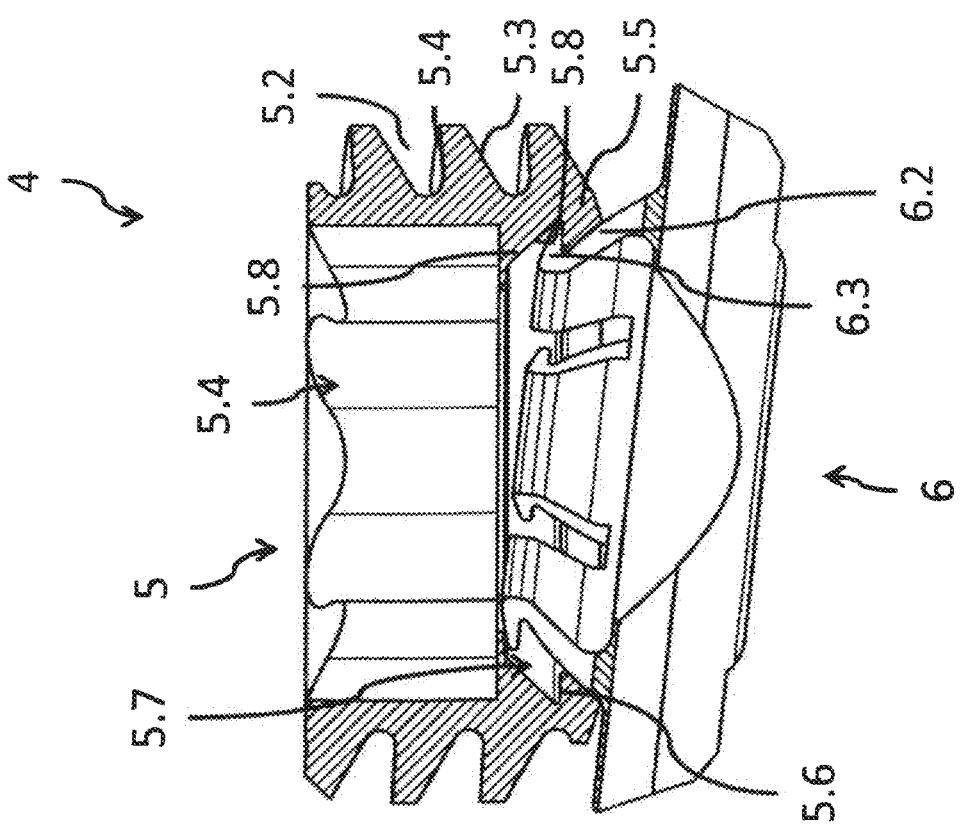
FIG. 10 is a longitudinal sectional view of the clamping device according to FIG. 8 with a tilted rod clamp.

Based on the dimensioning of the inner cone 5.8 of the tightening screw 5, a tilting motion of the rod clamp 6 in the tightening screw 5 is possible, as this is shown in FIGS. 10 and 11 with a tilt angle of about 6° in relation to the symmetry axis S of the tightening screw 5. Due to the embodiment of the proximally tapering inner cone 5.8, the bosses 6.3 of the rod clamp 6 are in contact with the inner wall of the inner cone 5.8 in the tilted position of the rod clamp 6 as well. The radial fixation of the rod clamp 6 is guaranteed in this manner in the axially oriented position and in the tilted position. FIG. 11 shows an axial section of the clamping device 4 according to FIG. 10 rotated by 90°.

As was stated, FIGS. 1 through 4 show a multiaxial embodiment of the fixating device 1. This has, further, a multiaxial pressing element 9 (FIGS. 12-14) and this described pedicle screw 2 with a spherical screw head 2.3 (FIGS. 15, 16).

The multiaxial pressing element 9 (FIGS. 12-14) has on its proximal side a partially cylindrical recess 9.1 for partially enclosing or receiving the rod 10, while another hemispherical or dome-shaped recess 9.2 is provided on the distal end face of the pressing element 9 in order to grasp the spherical screw head 2.3 of the pedicle screw 2.

The pressing element 9, which is the distal pressing element in relation to the rod 10, has a jacket 9.4 tapering from its distal end towards the proximal end, so that a gap 9.5 is formed between this and the inner wall of the tulip 3 (see especially in FIG. 3).

Tilting of the pressing element 9 within the tulip 3 in relation to an axially oriented central position is possible as a result. The pressing element 9 can thus assume a tilted orientation made possible for the rod 10 by the clamping device 4 described and it can be tightened in this position, namely, both in an orientation offset angularly in relation to the orientation of the mutually opposite elongated holes 3.2 in the walls of the tulip 3 and in an orientation tilted in relation to the vertical axis. The clamping device 4 thus makes possible such tilted orientations of the rod 10 and does not hinder these.

The partially cylindrical recess 9.1 has a larger radius of curvature than the rod 10 shown in FIG. 3. As a result, a clearance 9.6 is obtained at right angles to the extension of the rod 10 at the proximal opening of the pressing element 9 at about half of the height of the rod 10. As a result, rods 10 with different diameters can be inserted into the same fixating device 1. If the rod shown has, for example, a diameter of 5.5 mm, as it is used and is common in most patients, and the cylindrical recess has a diameter of 6 mm, a rod with a diameter of 6 mm can also be inserted, for example, in more robust, especially young patients, in whom a rod with a diameter of 5.5 mm often lacks the necessary strength.

Two mutually opposite, recessed pressing surfaces 9.3 are provided on the radial outer side of the pressing element 9 in the distal area for cross bolts 3.5 which can be screwed in radially from the outside through the tulip 3 for fixing the pressing element 9 within the tulip 3.

The multiaxial pedicle screw 2 itself is shown in FIGS. 15 and 16 and has—as was already mentioned above—the spherical pedicle screw head 2.3. The pedicle screw head 2.3 is pivotable in all directions in the dome-shaped recess 9.2 at the distal area of the multiaxial pressing element 9. The screw head 2.3 and hence the pedicle screw 2 are held—securely—by means of the pressing element 9 in the tulip 3, because this has a narrowed opening at its distal end 3.3 compared to the diameter of the screw head (FIGS. 1-4).

Especially the clamping device 4 with the tightening screw 5 and the rod clamp 6 is the same in a monoaxial device according to FIG. 17ff as in the above-described multiaxial fixating device. Only a—monoaxial—pedicle screw head 2.3a of the pedicle screw 2 and a—monoaxial—pressing element 9a, which are shown in enlarged views in FIGS. 19-24, are different.

Figure 19:
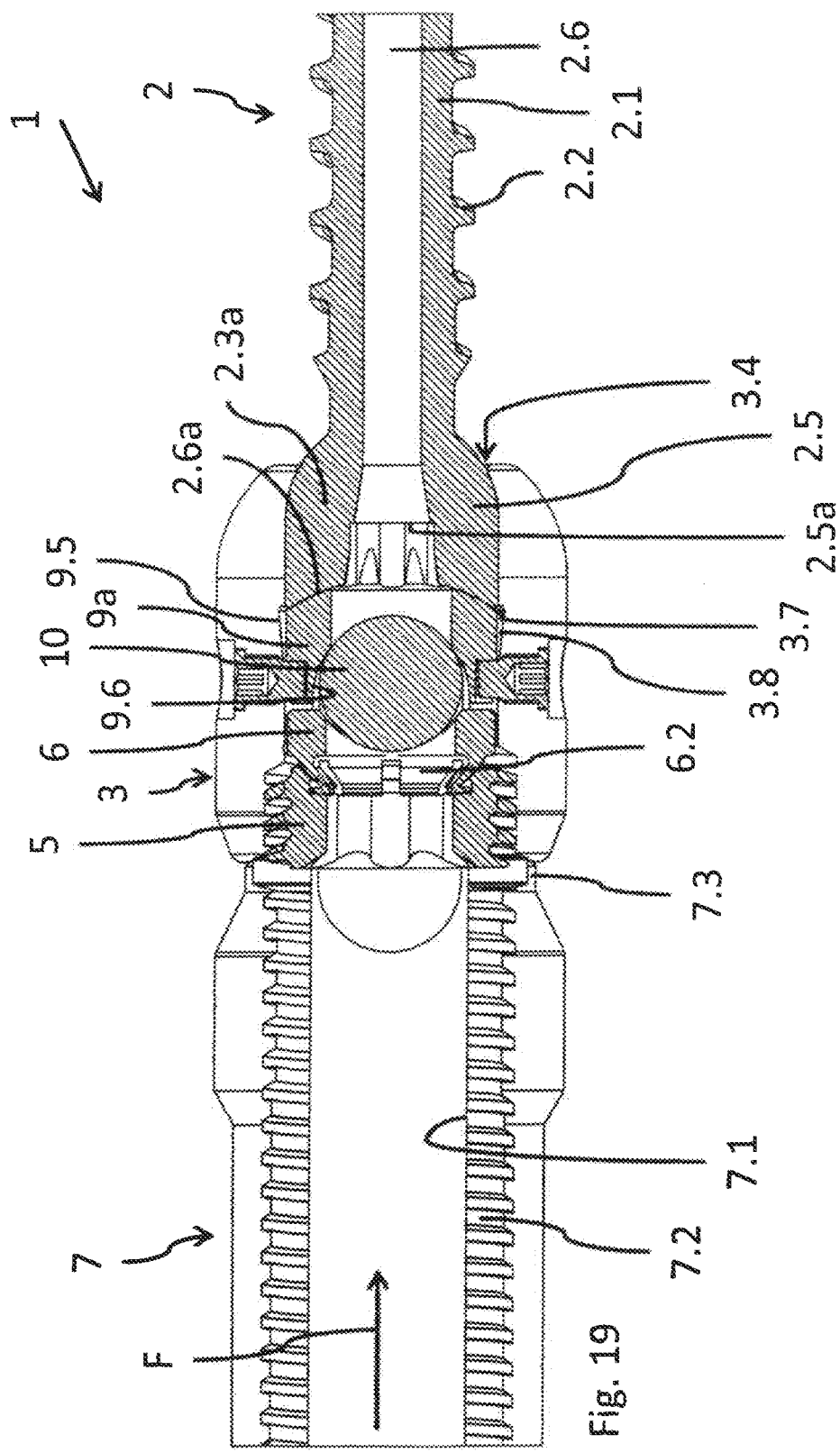
FIG. 19 is an enlarged sectional view of a part of the fixating device according to FIGS. 17 and 18.

FIGS. 17 through 19 show a monoaxial fixating device 1 in a lateral view (FIG. 17) and in a longitudinal section (FIGS. 18 and 19). Identical parts and features are designated, in principle, by the same reference numbers as in the case of the multiaxial embodiment according to FIGS. 1 through 16, to which reference is made. The different variants will be explained below.

The tulip 3 with the monoaxial pressing element 9 is seen distally from the clamped cross rod 10 in the clamping device 4 according to FIGS. 17 through 19. The pressing element 9 holds the pedicle screw head 2.3a, while the pedicle screw 2 itself is screwed into and fixed in a vertebral body (not shown). The tightening screw 5, which acts on the rod clamp 6 and which is screwed in the screwdown direction F along the internal thread 7.1 of the tulip extension 7 by means of a rotating tool (not shown), is located in the tulip 3 proximally from the cross rod 10. This tightening screw assumes here a tilted position and can thus hold the cross rod 10 at right angles in a multiaxial direction of extension.

The monoaxial pressing element 9a has, just like the multiaxial pressing element 9, a proximal, partially cylindrical recess 9.1 for partially receiving the rod 10, but, with a difference, a flat, frustoconical distal end face 9a.2 facing the screw head 2.3a of the pedicle screw 2 with a conical ring-shaped circumferential edge 9a.3, which encloses a central opening 9a.4 (FIGS. 20-22).

The inner wall of the tulip 3 has a shoulder 3.7 and, proximally behind this, an expansion 3.8, which tapers monoaxially in the proximal direction. In the monoaxial embodiment according to FIG. 17ff, the screw head 9a reaches proximally this shoulder 3.7 in the tulip 3. The—monoaxial—pressing element 9a begins distally only there and has at its distal end a smaller diameter than the expansion 3.8, so that a certain lateral clearance is present there and the monoaxial pressing element 9a can thus also easily be tilted in the tulip 3 in order thus not to hinder an eccentric orientation of the rod, which is allowed by the clamping device 4, as this is shown in FIG. 4 for the multiaxial device 1, but rather to assume it and to make it possible.

FIG. 22 shows the monoaxial pressing element 9a in a perspective view; the recess 9.1, which is expanded compared to the cross frame of the rod 10, makes possible an eccentric fixation of the rod 10.

As is shown especially in FIGS. 18, 23 and 24, the pedicle screw 2 has at its proximal end a—monoaxial—pedicle screw head 2.3a, which can correspondingly be pivoted. The screw head 2.3a has a cylindrical jacket 2.5 and a flat proximal end-face depression 2.5a, which jacket 2.5 has a likewise conical ring-shaped edge 2.6a adapted to the circumferential edge 9a.3 (FIGS. 19, 24).

While the pedicle screws 2 shown up to and including FIG. 22 have a double thread over the entire length of the screw shaft 2.1, the pedicle screw 2 shown in FIGS. 23 and 24 has a quadruple thread 2.2.1 in the proximal area of the screw shaft 2.1 over about one fourth of the length of the thread or screw shaft 2.1. Such an embodiment may also be provided in the case of a multiaxial pedicle screw according to FIGS. 1 through 4, 15 and 16.

While specific embodiments of the invention have been shown and described in detail to illustrate the application of the principles of the invention, it will be understood that the invention may be embodied otherwise without departing from such principles.

The invention claimed is:

1. A device for fixating a rod on a bone, the device comprising:
   a tulip rod mount;
   a pedicle screw;
   a tightening screw;
   a rod clamp pivotable to the tightening screw; and
   a rod clamp adapter connecting the tightening screw and the rod clamp, wherein the rod clamp adapter is a ring part with proximally radially outwardly directed projections, which mesh with radial incisions in the tightening screw with a clearance, wherein distal, likewise radially outwardly directed projections are predefined, which mesh with radial incisions of the rod clamp.

2. A device in accordance with claim 1, wherein the rod clamp and the tightening screw have bilateral spherical zones facing one another and oriented obliquely to a principal axis, via which bilateral spherical zones the rod clamp and the tightening screw are pivotable relative to one another.

3. A device in accordance with claim 1, wherein the tightening screw and the rod clamp have undercuts extending behind one another.

4. A device in accordance with claim 3, wherein the undercut of the tightening screw is formed by a ring projection.

5. A device in accordance with claim 3, wherein the undercuts of the rod clamp are formed by more than two elastic fingers with bosses, which fingers are arranged over the circumference.

6. A device in accordance with claim 3, wherein the tightening screw has an inner cone tapering conically in the proximal direction away from the undercut.

7. A device in accordance with claim 1, wherein the rod clamp and the rod clamp adapter are welded together.

8. A device in accordance with claim 1, wherein the rod clamp has a partially circular clamping recess on a rod clamp side facing away from the tightening screw.

9. A device in accordance with claim 8, wherein a flank of the thread of the tightening screw, which flank is directed proximally in relation to the screwdown direction, extends at an angle smaller than or equal to 5°, to a radial plane to the symmetry axis of the tightening screw.

10. A device in accordance with claim 8, wherein a flank of the thread of the tightening screw, which flank is directed distally in the screwdown direction, extends at an angle different from 90° to the symmetry axis of the tightening screw, preferably by 30°, to a radial plane.

11. A device in accordance with claim 1, wherein the tightening screw has an asymmetric tightening screw thread.

12. A device in accordance with claim 1, wherein the tightening screw has a plurality of depressions or a non-cylindrical depression on a tightening screw side facing away from the rod clamp.

13. A device in accordance with claim 1, further comprising a pressing element, which is mounted opposite the rod clamp in the tulip rod mount.

14. A device in accordance with claim 13, wherein the pressing element is mounted tiltably in the rod mount.

15. A device in accordance with claim 14, wherein a diameter of the pressing element is reduced on at least one end faces thereof compared to an internal diameter of the rod mount.

16. A device in accordance with claim 1, wherein a screw shaft of the pedicle screw has a double thread, wherein a proximal area of the screw shaft is configured as a quadruple thread over a length of one fourth of the pedicle screw shaft.

17. A device for fixating a rod on a bone, the device comprising:
   a tulip rod mount;
   a pedicle screw;
   a tightening screw;
   a rod clamp pivotable to the tightening screw; and
   a pressing element, which is mounted opposite the rod clamp in the tulip rod mount, wherein the pressing element of the rod mount tapers from a distal end face thereof to a proximal end face, so that there is a radial clearance proximally between the inner wall of the rod mount and the jacket of the pressing element or that the inner wall of the rod mount expands from the level of the proximal end face of the pressing element to the level of the distal end face of the pressing element while a radial clearance is guaranteed between the pressing element and the rod mount at the level of the distal end face of the pressing element.

18. A device in accordance with claim 17, wherein the rod clamp and the tightening screw have bilateral spherical zones facing one another and oriented obliquely to a principal axis, via which bilateral spherical zones the rod clamp and the tightening screw are pivotable relative to one another.

19. A device in accordance with claim 17, wherein the tightening screw and the rod clamp have undercuts extending behind one another.

20. A device in accordance with claim 19, wherein the undercut of the tightening screw is formed by a ring projection.

21. A device in accordance with claim 19, wherein the undercuts of the rod clamp are formed by more than two elastic fingers with bosses, which fingers are arranged over the circumference.

22. A device in accordance with claim 19, wherein the tightening screw has an inner cone tapering conically in the proximal direction away from the undercut.

23. A device in accordance with claim 19, further comprising a rod clamp adapter connecting the tightening screw and the rod clamp.

24. A device in accordance with claim 23, wherein the rod clamp adapter is a ring part with proximally radially outwardly directed projections, which mesh with radial incisions in the tightening screw with a clearance, wherein distal, likewise radially outwardly directed projections are predefined, which mesh with radial incisions of the rod clamp.

25. A device in accordance with claim 23, wherein the rod clamp and the rod clamp adapter are welded together.

26. A device in accordance with claim 17, wherein the rod clamp has a partially circular clamping recess on a rod clamp side facing away from the tightening screw.

27. A device in accordance with claim 26, wherein a flank of the thread of the tightening screw, which flank is directed proximally in relation to the screwdown direction, extends at an angle smaller than or equal to 5°, to a radial plane to the symmetry axis of the tightening screw.

28. A device in accordance with claim 26, wherein a flank of the thread of the tightening screw, which flank is directed distally in the screwdown direction, extends at an angle different from 90° to the symmetry axis of the tightening screw, preferably by 30°, to a radial plane.

29. A device in accordance with claim 17, wherein the tightening screw has an asymmetric tightening screw thread.

30. A device in accordance with claim 17, wherein the tightening screw has a plurality of depressions or a non-cylindrical depression on a tightening screw side facing away from the rod clamp.

31. A device in accordance with claim 30, wherein the pressing element is mounted tiltably in the rod mount.

32. A device in accordance with claim 31, wherein a diameter of the pressing element is reduced on at least one end faces thereof compared to an internal diameter of the rod mount.

33. A device in accordance with claim 17, wherein a screw shaft of the pedicle screw has a double thread, wherein a proximal area of the screw shaft is configured as a quadruple thread over a length of one fourth of the pedicle screw shaft.

\* \* \* \* \*